United States Patent [19]
Rizzardo et al.

[11] Patent Number: 5,977,278
[45] Date of Patent: Nov. 2, 1999

[54] POLYMERS FORMED FROM ALLYLIC CHAIN TRANSFER AGENTS

[75] Inventors: Ezio Rizzardo, Wheelers Hill; San Hoa Thang, Clayton South; Graeme Moad, Kallista, all of Australia; Charles T. Berge, Rochester Hills, Mich.

[73] Assignees: E. I. du Pont de Nemours and Company, Wilmington, Del.; Commonwealth Scientific and Industrial Research Organisation, Campbell, Australia

[21] Appl. No.: 09/074,438

[22] Filed: May 7, 1998

Related U.S. Application Data

[62] Division of application No. 08/635,907, filed as application No. PCT/AU94/00672, Nov. 2, 1994, Pat. No. 5,773,543.

[51] Int. Cl.$^6$ ...................................................... C08F 2/38
[52] U.S. Cl. .................... 526/319; 526/215; 526/318; 526/327; 526/328; 526/329.7; 526/335; 526/346; 526/347.1
[58] Field of Search ................................... 526/215, 318, 526/319

[56] References Cited

U.S. PATENT DOCUMENTS

| | | | |
|---|---|---|---|
| 4,322,491 | 3/1982 | Sander et al. | 430/286 |
| 4,692,493 | 9/1987 | Sulzbach | 524/805 |
| 5,010,189 | 4/1991 | Herold et al. | 544/174 |
| 5,264,530 | 11/1993 | Darmon | 526/194 |
| 5,362,826 | 11/1994 | Berge et al. | 526/194 |
| 5,385,996 | 1/1995 | Rizzardo et al. | 526/240 |

FOREIGN PATENT DOCUMENTS

| | | |
|---|---|---|
| B191457/76 | 7/1979 | Australia . |
| B-83396/87 | 4/1987 | Australia . |
| 1 556 999 | 12/1979 | European Pat. Off. . |
| J52 111509A | 9/1977 | Japan . |
| WO 91/06535 | 5/1991 | WIPO . |
| WO91/06535 | 5/1991 | WIPO . |
| WO 93/22355 | 11/1993 | WIPO . |

OTHER PUBLICATIONS

Sumitomo Kagaku Kogya K.K., Patent Abstracts of Japan (Abstract, formula (III)), JP,A,52–111509, C–77, 3813, Sep. 19, 1997.

Takashi Tsuda and Lon J. Mathias, New Dicyano–Containing Cyclopolymers Having High Stereoregularity Derived from Dimethacrylmalononitrile, *Macmomolecules*, 26, 6359–6363, 1993.

International Search Report, International Application No. PCT/AU94/00672, Feb. 10, 1995.

*Primary Examiner*—Fred Zitomer
*Attorney, Agent, or Firm*—James A. Costello; Sudhir G. Deshmukh

[57] ABSTRACT

The present invention relates to polymers having the formula:

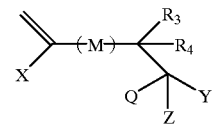

wherein:
M, Q, X, Y, Z, $R^3$ and $R^4$ are as defined in the text.

17 Claims, No Drawings

POLYMERS FORMED FROM ALLYLIC CHAIN TRANSFER AGENTS

CROSS-REFERENCE TO RELATED APPLICATIONS

This is a divisional of application Ser. No. 08/635,907 filed on Aug. 1, 1996, now U.S. Pat. No. 5,773,543, which is a 371 of PCT/Au94/00672 filed on Nov. 2, 1994, now abandoned.

BACKGROUND OF THE INVENTION

This invention relates to polymers formed by the radical-initiated polymerization of unsaturated species of low molecular weight. Polymers of low molecular weight, or oligomers, are important as precursors in producing other polymeric materials and such polymers have been found to be useful in a variety of products, for example, in the production of high solids (low VOC) surface coatings, in adhesives and as plasticizers in polymeric composites.

In conventional polymerization practice, the manufacture of oligomers requires the use of an initiator which acts as a free radical source, and of a chain transfer agent. The chain transfer agent controls the molecular weight of the polymer by reacting with the propagating polymer radical to terminate its growth. It then initiates a new polymer chain thus transferring the growth process from one discrete polymer molecule to another discrete polymer molecule. The most commonly used chain transfer agents are alkanethiols, which normally are associated with an objectionable odor and lead to a wide distribution of molecular weight with certain monomers. Also, the residual thiols and the end thio-ether linkage of the polymers may have an adverse effect on the properties of the ultimate product from the polymer.

The polymers of the present invention are prepared without the disadvantages of polymerizations regulated with thiols by using alternative polymerization regulators. These regulators have good stability and shelf life while maintaining many of the advantages over thiols. In the majority of cases, the materials that are part of the present process present a different range of chain transfer activities, allowing more opportunity for an optimal process to be selected for a given polymerization system of monomers and polymerization conditions. The chain transfer constant that a given regulator possesses is an important consideration in selecting the optimum process for producing low molecular weight polymers.

SUMMARY OF THE INVENTION

This invention concerns polymers made by the free radical polymerization of unsaturated monomers. The polymers have low molecular weight and narrow polydispersity and are prepared employing the chain transfer agents of Formula I:

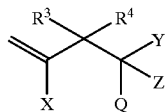

Formula (I)

wherein,

X is selected from hydrogen; CN; optionally substituted aryl; COOH; COOR; $C(O)NHR^6$; $C(O)NR^7R^8$; and halogen;

Q is selected from $COOR^1$; CN; $C(O)NR^7R^8$;

Y is selected from hydrogen; $C_1$ to $C_6$ alkyl; $C_1$ to $C_6$ alkyl substituted with one or more substituents selected from hydroxy, amino, $C_1$ to $C_6$ alkoxy, $C_1$ to $C_6$ alkoxycarbonyl, halogen, CN, and optionally substituted aryl; $C_1$ to $C_6$ alkenyl; and $C_1$ to $C_6$ alkynyl;

Z is selected from $COOR^2$; CN; and optionally substituted aryl;

$R^3$, $R^4$ are the same or different and are selected from hydrogen, $C_1$ to $C_4$ alkyl, alkyl and halogen; or $R^3$ and $R^4$ together with the carbon atom to which they are attached form part of a carbocyclic or heterocyclic ring structure;

R is selected from $C_1$ to $C_{18}$ alkyl; $C_1$ to $C_{12}$ alkyl substituted with one or more substituents selected from hydroxy, amino, $C_1$ to $C_6$ alkoxy, phenyl, halogen, NCO, CN, and $COOR^5$;

$R^1$, and $R^2$ are the same or different and are selected from $C_1$ to $C_{18}$ alkyl; $C_1$ to $C_{12}$ alkyl substituted with one or more substituents selected from hydroxy, $C_1$ to $C_6$ acyloxy, $C_1$ to $C_6$ alkoxy, amino, halogen, $Si(R^9)_3$, $Si(OR^9)_3$, optionally substituted aryl, CN, NCO;

$R^5$ is selected from hydrogen and $C_1$ to $C_6$ alkyl;

$R^6$ is selected from hydrogen, and $C_1$ to $C_{18}$ alkyl;

$R^7$, and $R^8$ are the same or different and are selected from $C_1$ to $C_{18}$ alkyl; and $R^9$ is selected from $C_1$ to $C_{18}$ alkyl; $C_1$ to $C_{18}$ cycloalkyl; and optionally substituted aryl.

A preferred group of compounds of Formula (I) are the malonates with $Q=COOR^1$ and $Z=COOR^2$ having the Formula (IA)

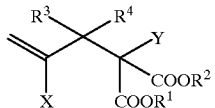

(Formula IA)

Wherein:

X is selected from hydrogen; CN; optionally substituted aryl; COOH; COOR; $C(O)NHR^6$; $C(O)NR^7R^8$; and halogen;

Y is selected from hydrogen; $C_1$ to $C_6$ alkyl; $C_1$ to $C_6$ alkyl substituted with one or more substituents selected from hydroxy, amino, $C_1$ to $C_6$ alkoxy, $C_1$ to $C_6$ alkoxycarbonyl, halogen, CN, optionally substituted aryl; $C_1$ to $C_6$ alkenyl; $C_1$ to $C_6$ alkynyl;

$R^1$, and $R^2$ are the same or different and are selected from $C_1$ to $C_{18}$ alkyl; $C_1$ to $C_{12}$ alkyl substituted with a substituent selected from hydroxy, $C_1$ to $C_6$ acyloxy, $C_1$ to $C_6$ alkoxy, amino, halogen, optionally substituted aryl, CN, and NCO;

$R^3$, and $R^4$ are the same or different and are selected from hydrogen, $C_1$ to $C_4$ alkyl, and halogen; and R, $R^6$, $R^7$ and $R^8$ are as defined above.

Another preferred group of compounds which possess high chain transfer activities are the compounds of Formula (IB) where $Q=COOR^1$ and Z is optionally substituted aryl:

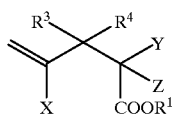

(Formula IB)

wherein:

X, Y, R¹, R³ and R⁴ are as defined above; and Z is optionally substituted aryl.

This invention concerns a polymer formed from at least one unsaturated monomer, M, selected from the group consisting of units from acrylic esters, methacrylic esters, vinyl esters, vinyl aromatics and unsaturated hydrocarbons, having the formula:

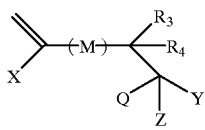

wherein:

X is selected from hydrogen; CN; optionally substituted aryl; COOH; COOR; C(O)NHR⁶; C(O)NR⁷R⁸; and halogen;

Q is selected from COOR¹; CN; C(O)NR⁷R⁸;

Y is selected from hydrogen; $C_1$ to $C_6$ alkyl; $C_1$ to $C_6$ alkyl substituted with one or more substituents selected from hydroxy, amino, $C_1$ to $C_6$-alkoxy, $C_1$ to $C_6$ alkoxycarbonyl, halogen, CN, and optionally substituted aryl; $C_1$ to $C_6$ alkenyl; and $C_1$ to $C_6$ alkynyl;

Z is selected from COOR²; CN; C(O)NR⁷R⁸; and optionally substituted aryl;

R³, R⁴ are the same or different and are selected from hydrogen, $C_1$ to $C_4$ alkyl, alkyl and halogen; together with the carbon atom to which they are attached form part of a carbocyclic or heterocyclic ring structure;

R is selected from $C_1$ to $C_{18}$ alkyl; $C_1$ to $C_{12}$ alkyl substituted with one or more substituents selected from hydroxy, amino, $C_1$ to $C_6$ alkoxy, phenyl, halogen, NCO, CN, and COOR⁵;

R¹, and R² are the same or different and are selected from $C_1$ to $C_{18}$ alkyl; $C_1$ to $C_{12}$ alkyl substituted with one or more substituents selected from hydroxy, $C_1$ to $C_6$ acyloxy, $C_1$ to $C_6$ alkoxy, amino, halogen, Si(R⁶)₃, Si(OR⁹)₃, optionally substituted aryl, CN, NCO;

R⁵ is selected from hydrogen and $C_1$ to $C_6$ alkyl;

R⁶ is selected from hydrogen, and $C_1$ to $C_{18}$ alkyl;

R⁷, and R⁸ are the same or different and are selected from $C_1$ to $C_{18}$ alkyl; and R⁹ is selected from the group consisting of $C_1$ to $C_{18}$ alkyl; $C_1$ to $C_{18}$ cycloalkyl; and optionally substituted aryl.

This invention concerns a preferred polymer:

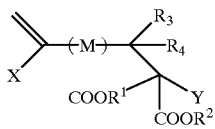

wherein:

X is selected from hydrogen; CN; optionally substituted aryl; COOH; COOR; C(O)NHR⁶; C(O)NR⁷R⁸; and halogen;

Y is selected from hydrogen; $C_1$ to $C_6$ alkyl; $C_1$ to $C_6$ alkyl substituted with one or more substituents selected from hydroxy, amino, $C_1$ to $C_6$ alkoxy, $C_1$ to $C_6$ alkoxycarbonyl, halogen, CN, optionally substituted aryl; $C_1$ to $C_6$ alkenyl; $C_1$ to $C_6$ alkynyl;

R¹, and R² are the same or different and are selected from $C_1$ to $C_{18}$ alkyl; $C_1$ to $C_{12}$ alkyl substituted with a substituent selected from hydroxy, $C_1$ to $C_6$ acyloxy, $C_1$ to $C_6$ alkoxy, amino, halogen, optionally substituted aryl, CN, and NCO; and R³, and R⁴ are the same or different and are selected from hydrogen, $C_1$ to $C_4$ alkyl, and halogen.

This invention concerns a most preferred polymer:

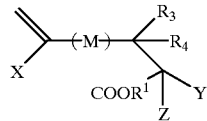

wherein Z is substituted or unsubstituted aryl. Also of concern are the polymers described above wherein at least one monomer is selected from the group consisting of methyl acrylate, ethyl acrylate, butyl acrylate, 2-ethylhexyl acrylate, methyl methacrylate, ethyl methacrylate, n-butyl methacrylate, 2-ethylhexyl methacrylate, vinyl acetate, styrene, p-chloromethylstyrene, 2-vinylpyridine, 4-vinylpyridine, N-vinylpyrrolidone, vinyl halide of the formula $CH_2=CHX$ where X is Cl or F, vinylidene halide of the formula $CH_2=CX_2$ wherein X is independently Cl or F, vinyl ethers $CH_2=CHOR$ where R is alkyl, allyl ether, allyl carbonate, and diallyl carbonate.

DETAILS OF THE INVENTION

The term "optionally substituted aryl" is used herein to mean an aromatic carbocyclic group which can be substituted with one or more substituents that do not interfere with the polymerization process. Such substituents include alkyl, hydroxyalkyl, aminoalkyl, carboxylic acid, ester, acyloxy, amide, nitrile, haloalkyl, alkoxy, phosphonate, sulfonate, silyl or silyloxy groups. Preferred aryl groups are phenyl or naphthyl groups. When X is halogen, chlorine or bromine are preferred. When R³ or R⁴ is halogen, chlorine or fluorine are preferred.

The following compounds of Formula I are preferred.
ethyl 2,4-bis(ethoxycarbonyl)-2-methyl-4-pentenoate
ethyl 2,4-bis(ethoxycarbonyl)-2-ethyl-4-pentenoate
ethyl 2-benzyl-2,4-bis(ethoxycarbonyl)-4-pentenoate
ethyl 2-ethoxycarbonyl-2-methyl-4-phenyl-4-pentenoate
ethyl 2-ethoxycarbonyl-2,3-dimethyl-4-(t-butoxycarbonyl)-4-pentenoate
ethyl 2-phenyl-4-(t-butoxycarbonyl)-4-pentenoate.

The process employs compounds of Formula (I) as alternatives to thiols or other chain transfer agents for the control of molecular weight and is operated in a similar manner to conventional processes using thiols. The compounds of Formula I can be prepared easily from inexpensive starting materials. Unlike thiols, they do not, in general, possess an objectionable odor.

The process is operated employing the appropriate quantity of at least one compound of Formula (I) in place of a prior art used thiol. The proportion of compound of Formula (I) used is in the range of 0.01 to 30 mole percent based on total monomer, with a preferred range of 0.1 to 10 mole percent.

The process is operated at any of the reaction conditions appropriate to free radical polymerization, i.e., temperatures from −100° C. to 200° C. and pressures from below atmospheric to substantially above atmospheric.

The polymerization process can be carried out in bulk, solution, emulsion, suspension or other conventional polymerization modes. Source of radicals for polymerizations are well known in the art and they include (α,α'-azobisisobutyronitrile, 4,4'-azobis(4-cyanovaleric acid), 2,2'-azobis(2,4-dimethylpentanenitrile), benzoyl peroxide, t-butyl peroxybenzoate, ammonium persulfate, potassium persulfate.

Any unsaturated monomers susceptible to free radical polymerization can be used although it should be noted that the chain transfer constant will vary with the monomer used. Suitable unsaturated monomers include acrylic esters, methacrylic esters, vinyl esters, vinyl aromatics, unsaturated (includes polyunsaturated) hydrocarbons, or mixtures of these. Examples of these monomers are methyl acrylate, ethyl acrylate, butyl acrylate, 2-ethylhexyl acrylate, methyl methacrylate, ethyl methacrylate, n-butyl methacrylate, 2-ethylhexyl methacrylate, vinyl acetate, styrene, p-chloromethylstyrene, 2-vinylpyridine, 4-vinylpyridine, N-vinylpyrrolidone, vinyl halides of the formula $CH_2=CHX$ where X is Cl or F, vinylidene halides of the formula $CH_2=CX_2$ wherein X is independently Cl or F, vinyl ethers $CH_2=CHOR$ where R is alkyl, and allyl monomers such as allyl ethers, allyl carbonates or diallyl carbonates.

Compounds of general Formula (I) display an unexpected high activity in controlling molecular weight in polymerization reactions and have chain transfer constants superior to those of thiols, particularly with styrene and acrylates. Their activity is such that their chain transfer constants can approach the optimum values of 1.0 for batch polymerizations and this activity is not as highly dependent as that of thiols on the structure of the propagating radical.

The process is applicable to the manufacture of synthetic rubbers, and other polymer formulations where reduced molecular weight aids processing and improves properties. The process can also be used to produce low molecular weight polymers, oligomers, macromonomers and functional polymers for a variety of applications such as high-solids surface coatings, paints, and adhesives. Furthermore, the process can be used to enable better control over the polymerization kinetics, e.g., delaying the onset of gelation in cross-linking systems.

Good chain transfer activities are provided by the compound ethyl 2,4-bis(ethoxycarbonyl)-2-methyl-4-pentenoate (Ib) which possesses significantly higher activity than the methyl 4-methoxycarbonyl-2,2-dimethyl-4-pentenoate (MMA dimer or dimethyl 2,2-dimethyl-4-methylene glutarate) (refer to Table 5) in methyl methacrylate, acrylate and styrene polymerizations.

EXAMPLES
Preparation of Chain Transfer Agents

The allylic malonate derivatives [(Formula IA)] are synthesized in good to excellent yield in a one-step reaction between the corresponding allylic halides (II) and malonates (IIIA). The reaction is carried out in the presence of base and solvent. Acetonitrile, N,N-dimethylformamide (DMF), dried THF or diethyl ether are suitable solvents. Although many (inorganic and organic) bases are suitable, sodium hydride, sodium alkoxide, sodamide, potassium alkoxides are preferred bases. The use of sodium hydride is found to provide better results than sodium alkoxide for the synthesis of these types of compounds.

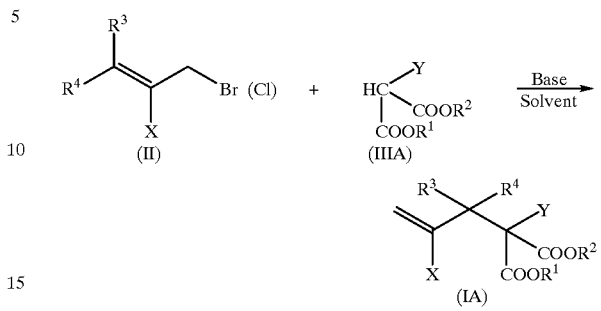

Similarly, the allylic compounds of Formula IB [e.g., compound (Ii)] can be synthesized in good yield in a one-step reaction between the corresponding allylic halide (II) and arylacetate (IIIB). The reaction is carried out in the presence of base and solvent.

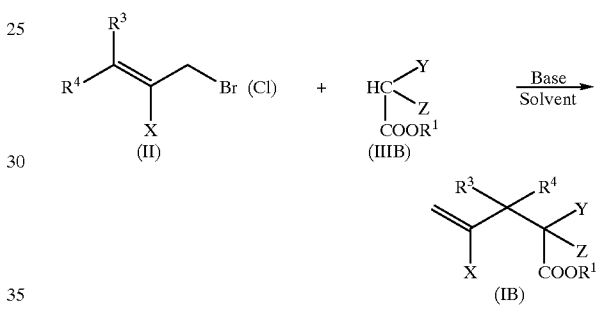

Typical compounds (Ia & Ib) and their preparation are further illustrated by the following preparative examples.

PREPARATION 1

Ethyl 2,4-bis(ethoxycarbonyl)-4-pentenoate (Ia) [Formula (IA), $X=COOCH_2CH_3$; $Y=R^3=R^4=H$; $R^1=R^2=CH_2CH_3$].

[Typical procedure].

To a suspension of sodium hydride (80% dispersion in oil, 0.36 g, 12 mmol) in acetonitrile (10 mL), was added diethyl malonate (1.60 g, 10 mmol). The resulting suspension was allowed to stir at room temperature for 15 minutes. A solution of ethyl a-(bromomethyl)acrylate [obtained from a modified procedure of S. E. Drewes, G. Loizou and G. H. P. Roos, *Synthetic Communications*, 1987, 17(3), 291–298] (1.93 g, 10 mmol) in acetonitrile (5 mL) was then added slowly to the above suspension. Stirring was maintained for 2 hours and then the reaction mixture was poured into water, and extracted (3×) with diethyl ether. The extracts were combined and dried over anhydrous $Na_2SO_4$, filtered and evaporated to dryness. Distillation of the crude product under reduced pressure gave (Ia) as a colorless liquid (b.p.~140° C./0.1 mmHg) (1.90 g,~70%). $^1$H-NMR (CDCl$_3$) d(ppm) 1.21 (t, 6H), 1.25 (t, 3H), 2.85 (d, 2H), 3.67 (t, 1H), 4.15 (q, 4H), 4.20 (q, 2H), 5.60 (br. s, 1H) and 6.18 (br. s, 1H). $^{13}$C-NMR (CDCl$_3$) δ(ppm) 13.98, 31.34, 50.76, 60.81, 61.37, 127.56, 136.68, 166.38 and 168.67.

PREPARATION 2

Ethyl 2,4-bis(ethoxycarbonyl)-2-methyl-4-pentenoate (Ib)

[Formula (IA), X=COOCH$_2$CH$_3$; Y=CH$_3$; R$^3$=R$^4$=H; R$^1$=R$^2$=CH$_2$CH$_3$].

This compound was prepared using a similar procedure to that described above. Pure ethyl 2,4-bis(ethoxycarbonyl)-2-methyl-4-pentenoate (Ib) was obtained (60% yield) after column chromatography on silica-gel (diethyl ether: n-hexane 1:4 as eluent). $^1$H-NMR (CDCl3) δ(ppm) 1.20 (t, 6H), 1.25 (t, 3H), 1.33 (s, 3H), 2.95 (s, 2H), 4.15 (m, 6H), 5.56 (br. s, 1H) and 6.22 (br. s, 1H). $^{13}$C-NMR (CDCl$_3$) δ(ppm) 13.91, 14.06, 35.98, 53.88, 60.78, 61.23, 128.61, 136.29, 166.67 and 171.57.

PREPARATION 3

Ethyl 2,4-bis(ethoxycarbonyl)-2-ethyl-4-pentenoate (Ic)

[Formula (IA), X=COOCH$_2$CH$_3$; Y=CH$_2$CH$_3$; R$^3$=R$^4$=H; R$^1$=R$^2$=CH$_2$CH$_3$].

This compound was prepared in ~80% yield using a similar procedure to that described in Example 1. $^1$H-NMR (CDCl$_3$) δ(ppm) 0.85 (t, 3H), 1.20 (t, 6H), 1.30 (t, 3H), 1.85 (q, 2H), 2.95 (s, 2H), 4.15 (m, 6H), 5.58 (br. s, 1H) and 6.25 (br. s, 1H). $^{13}$C-NMR (CDCl$_3$) δ(ppm) 8.58, 14.06, 14.16, 25.46, 32.98, 58.32, 60.89, 61.15, 128.42, 136.53, 167.05 and 171.09.

PREPARATION 4

Ethyl 2-benzal-2,4-bis(ethoxycarbonyl)-4-nentenoate (Id)

[Formula (IA), X=COOCH$_2$CH$_3$; Y=CH$_2$C$_6$H$_5$; R$^3$=R$^4$=H; R$^1$=R$^2$=CH$_2$CH$_3$].

This compound was prepared by a procedure similar to Example 1, using diethyl benzylmalonate as the starting material; the product was isolated in 76% yield as a colorless syrup. $^1$H-NMR (CDCl$_3$) δ(ppm) 1.20 (t, 6H), 1.30 (t, 3H), 2.95 (s, 2H), 3.25 (s, 2H), 4.15 (m, 6H), 5.65 (br. s, 1H), 6.25 (br. s, 1H) and 7.20 (m, 5H). $^{13}$C-NMR(CDCl$_3$) δ(ppm) 13.82, 14.11, 30.40, 39.63, 43.30, 58.75, 60.84, 61.20, 126.87, 128.11, 128.55, 130.08, 167.40 and 170.56.

PREPARATION 5

Ethyl 4-chloro-2-ethoxycarbonyl-2-methyl-4-pentenoate (Ie)

[Formula (IA), X=Cl; Y=CH$_3$; R$^3$=R$^4$=H; R$^1$=R2=CH$_2$CH$_3$].

To a suspension of sodium hydride (25.2 g, 0.84 moles, 80% dispersion in oil) and diethyl methylmalonate (104.5 g, 0.60 moles) in acetonitrile (500 mL), a solution of 2,3-dichloropropene (66.6 g, 0.60 moles) in acetonitrile (100 mL) was added slowly over 20 minutes with stirring at room temperature. The resulting mixture was allowed to stir at room temperature overnight. Water (250mL) was added, and the mixture extracted three times with diethyl ether (200 mL×3). The combined organic layers were washed successively with water (200 mL) and brine (200 mL), they were then dried over anhydrous MgSO$_4$. After removal of the organic solvent, distillation of the crude product under reduced pressure afforded the product (Ie) as a colorless liquid (91.6 g, 61.5% yield), b.p. 77–78° C. (0.1 mmHg). $^1$H-NMR (CDCl$_3$) δ(ppm) 1.22 (t, 6H), 1.42 (s, 3H), 3.00 (s, 2H), 4.18 (q, 4H), 5.20 (s, 1H) and 5.30 (s, 1H).

PREPARATION 6

Ethyl 2-ethoxycarbonyl-4-phenyl-4-pentenoate (If)

[Formula (IA), X=Phenyl; Y=R$^3$=R$^4$=H; R$^1$=R$^2$=CH$_2$CH$_3$].

This compound was prepared in ~20% yield (not optimized) according to a similar procedure to that described in Example 1. The reaction was carried out between a-(bromomethyl)styrene [obtained from the reaction of a-methylstyrene and N-bromosuccinimide in carbon tetrachloride according to the published procedure by H. Pines, H. Alul and M. Kolobielski, *J. Org Chem.*, 1957, 22, 1113-1114] and diethyl malonate in the presence of sodium hydride (1 eq.). $^1$H-NMR (CDCl$_3$) δ(ppm) 1.25 (t, 6H), 3.10 (d, 2H), 3.50 (t, 1H), 4.17 (q, 4H), 5.15 (br. s, 1H), 5.35 (br. s, 1H) and 7.35 (m, 5H).

PREPARATION 7

Ethyl 2-ethoxycarbonyl-2-methyl-4-phenvl-4-pentenoate (Ig)

[Formula (IA), X=Phenyl; Y=CH$_3$; R$^3$=R$^4$=H; R$^1$=R$^2$=CH$_2$CH$_3$].

This compound was prepared in ~60% yield by reacting a-(bromomethyl)styrene [obtained by method of H. Pines, H. Alul, M. Kolobielski, *J Org. Chem.*, p. 1113 (1957)] and diethyl methylmalonate in the presence of sodium hydride (2 eq.) in acetonitrile solvent. $^1$H-NMR (CDCl$_3$) δ(ppm) 1.10 (t, 6H), 1.30 (s, 3H), 3.18 (s, 2H), 3.90 (m, 4H), 5.10 (br. s, 1H), 5.27 (br. s, 1H) and 7.30 (m, 5H).

PREPARATION 8

Ethyl 2-ethoxycarbonyl-2,3-dimethyl-4-(t-butoxycarbonyl)-4-pentenoate (Ih)

[Formula (IA), X=COOC(CH$_3$)$_3$; Y=CH$_3$; R$^3$=H; R$^4$=CH$_3$; R$^1$=R$^2$=CH$_2$CH$_3$].

The starting material, t-butyl (Z)-2-bromomethyl-2-butenoate, was prepared via literature procedures [H. Hoffmann and J. Rabe, *Helvetica Chimica. Acta*, 67(2), p. 413 (1984)].

A stirred solution of diethyl methylmalonate (1.5 g, 8.6 mmol) in distilled THF was cooled to −5° C. and sodium hydride (0.52 g) added portionwise. The resultant suspension was stirred below 0° C. for an hour, then t-butyl (Z)-2-bromomethyl-2-butenoate added dropwise. The mixture was stirred below 0° C. for a further two hours before being allowed to warm to room temperature and stirred overnight. Solvent was removed under reduced pressure, water added and the product extracted with ether (3×50 ml), and the combined organic layers dried over anhydrous magnesium sulfate. Upon removal of ether under reduced pressure, a pale yellow oil was obtained (2.02 g, 72%). $^1$H-NMR spectrum revealed the presence of two isomers in a ratio of 4:1, with the preferred isomer being the major product (Ih). Column chromatography on silica gel (9:1, pet. spirit 40–60° C.: ethyl acetate) gave slight separation of the two isomers. The fraction containing the highest level of ethyl-2-ethoxycarbonyl-2,3-dimethyl-4-(t-butoxycarbonyl) pent-4-enoate (Ih) was used for the following spectroscopic data. $^1$H-NMR (CDCl$_3$) δ(ppm): 6.25, s, 1H; 5.55, s, 1H; 4.2, m, 4H; 3.7, q, 1H; 1.2–1.6, m, 21H. $^{13}$C-NMR (CDCl$_3$) δ(ppm): 171.7, 171.2, 166.6, 143.5, 125.2, 80.5, 61.1, 57.5, 36.7, 28.0, 17.5, 17.0, 14.0, 13.9.

PREPARATION 9

Ethyl 2-phenyl-4-(t-butoxycarbonyl)-4-pentenoate (Ii)

[Formula (IB), X=COOC(CH$_3$)$_3$; Y=R$^3$=R$^4$=H; R$^1$=CH$_2$CH$_3$; Z=phenyl]

The starting allylic bromide material, t-butyl 2-(bromomethyl)propenoate was prepared via a modified procedure of S. E. Drewes, G. Loizou and G. H. P. Roos, Synthetic Communications, 1987, 17(3), 291–298 in that the acrylate used was t-butyl acrylate.

Ethyl phenylacetate (6.66 g, 40.6 mmol) was dissolved in dry THF (20 mL) and sodium hydride (1.09 g, 36.5 mmol) added portionwise. The resulting suspension was stirred at room temperature for 30 minutes then cooled on ice while t-butyl 2-(bromomethyl)propenoate (4.49 g, 20.3 mmol) was added dropwise under nitrogen atmosphere. On completion of the addition, the reaction mixture was allowed to reach room temperature then heated under reflux for 8 hours. The THF solvent was removed under reduced pressure, water added and the product mixture extracted with diethyl ether (3×50 mL). After removal of organic solvent, the excess ethyl phenylacetate was removed by vacuum distillation and the residue was chromatographed on a silica-gel column using 5% ethyl acetate in petroleum spirit as eluent. The pure product (Ii) was obtained as a very pale yellowish liquid (2.5 g, 41%). $^1$H-NMR (CDCl$_3$) δ(ppm): 1.10, t, 3H; 1.45, s, 9H; 2.65, dd, 1H; 3.00, dd, 1H; 3.85, dd, 1H; 4.10, m, 2H; 5.35, s, 1H; 6.00, s, 1H; 7.25, s, 5H.

In the following examples, molecular weight measurements were performed on a Waters Associates liquid chromatograph equipped with differential refractometer and six m-styragel columns of 10$^6$, 10$^5$, 10$^4$, 10$^3$, 500 and 100 Å pore size. Tetrahydrofuran solvent was used at a flow rate of 1 mL/min. Results were derived by comparison with polystyrene standards using the Chromatix GPC-1 program.

The conversions were determined from the mass of the polymers isolated after precipitation in solvents where appropriate or after removal of all the volatiles in vacuo, and after subtracting the mass of the chain transfer agent.

Example 1
Polymerization of Methyl Methacrylate

α,α'-Azobisisobutyronitrile (23.4 mg) was dissolved in freshly distilled inhibitor-free methyl methacrylate (MMA) (25 mL). Aliquots (4 mL) were removed and added to ampoules containing weighed amounts of the allylic chain transfer agents of Formula (I). The contents of the ampoule were either degassed by three freeze-evacuate-thaw cycles and sealed under vacuum or by bubbling nitrogen through the solution. The mixtures were then polymerized at 60° C. for one hour. The contents of the ampoules were then added dropwise to methanol and the precipitated polymers were collected and dried in a vacuum oven to constant weight. A small portion of each polymer was examined by gel-permeation chromatography (GPC) to determine its molecular weight.

TABLE 1

Molecular Weight and Conversions for Methyl Methacrylate Polymerizations Carried Out in the Presence of Chain Transfer Agents (CTA).

| Entry | CTA | Temp. (° C.) | Time (hr.) | 10$^3$ [CTA]/ [Monomer] | % Conv. | M$_n$ # |
|---|---|---|---|---|---|---|
| 1 | Ia | 60 | 1.00 | 0.00 | 15.80 | 327160 |
| 2 | Ia | 60 | 1.00 | 10.20 | 14.70 | 287300 |
| 3 | Ia | 60 | 1.00 | 22.80 | 13.30 | 253630 |
| 4 | Ib | 60 | 1.00 | 0.00 | 14.95 | 159200 |
| 5 | Ib | 60 | 1.00 | 16.80 | 13.35 | 104100 |
| 6 | Ib | 60 | 1.00 | 31.30 | 12.80 | 89900 |
| 7 | Ib | 60 | 1.00 | 68.30 | 11.20 | 58700 |
| 8 | Ic | 60 | 1.00 | 0.00 | 16.30 | 254350 |
| 9 | Ic | 60 | 1.00 | 14.32 | 12.10 | 195900 |
| 10 | Ic | 60 | 1.00 | 28.37 | 9.95 | 190150 |
| 11 | Ic | 60 | 1.00 | 56.73 | 8.30 | 153150 |
| 12 | If | 60 | 1.00 | 0.00 | 14.72 | 266800 |
| 13 | If | 60 | 1.00 | 9.82 | 2.44 | 89000 |
| 14 | If | 60 | 1.00 | 19.64 | 1.30 | 64875 |
| 15 | If | 60 | 1.00 | 38.58 | 1.22 | 50800 |
| 16 | Ig | 60 | 1.00 | 0.00 | 11.49 | 299000 |
| 17 | Ig | 60 | 1.00 | 9.89 | 4.48 | 113400 |
| 18 | Ig | 60 | 1.00 | 19.03 | 0.42 | 91990 |
| 19 | Ig | 60 | 1.00 | 36.34 | 1.47 | 57530 |
| 20 | Ii | 60 | 1.00 | 0.00 | 12.74 | 248860 |
| 21 | Ii | 60 | 1.00 | 9.89 | 11.52 | 131020 |
| 22 | Ii | 60 | 1.00 | 18.15 | 11.61 | 100900 |
| 23 | Ii | 60 | 1.00 | 34.50 | 10.30 | 71120 |

Number-average molecular weight determined by GPC, calibrated with polystyrene standards.

Example 2
Polymerization of Styrene

Polymerizations of styrene (Sty) were carried out similarly for three hours at 60° C. α,α'-Azobisisobutyronitrile (21.6 mg) was dissolved in freshly distilled styrene (50 mL). Aliquots (10 mL) were removed and transferred to ampoules containing weighed amounts of chain transfer agent. After the degassing and polymerization, the contents of ampoules were poured into methanol and the precipitated polymers were collected, dried, and examined as before.

TABLE 2

Molecular Weight and Conversions for Styrene Polymerizations Carried Out in the Presence of Allylic Malonate Chain Transfer Agents and MMA Dimer (Methyl 4-methoxycarbonyl-2,2-dimethyl-4-pentenoate)

| Entry | CTA | Temp. (° C.) | Time (hr.) | 10$^3$ [CTA]/ [Monomer] | % Conv. | M$_n$ # |
|---|---|---|---|---|---|---|
| 1 | Ia | 60 | 3.00 | 0.00 | 9.80 | 130000 |
| 2 | Ia | 60 | 3.00 | 13.20 | 8.40 | 119250 |
| 3 | Ia | 60 | 3.00 | 26.20 | 9.30 | 114300 |
| 4 | Ib | 60 | 3.00 | 0.00 | 8.30 | 127000 |
| 5 | Ib | 60 | 3.00 | 14.86 | 4.20 | 20400 |
| 6 | Ib | 60 | 3.00 | 32.78 | 3.65 | 12500 |
| 7 | Ib | 60 | 3.00 | 43.11 | 3.20 | 11400 |
| 8 | Ih | 60 | 3.00 | 0.00 | 8.4 | 103995 |
| 9 | Ih | 60 | 3.00 | 8.75 | 6.3 | 43755 |
| 10 | Ih | 60 | 3.00 | 16.90 | 5.8 | 28222 |
| 11 | Ih | 60 | 3.00 | 30.40 | 5.2 | 18682 |
| 12 | Ii | 60 | 3.00 | 0.00 | 9.0 | 112525 |
| 13 | Ii | 60 | 3.00 | 9.01 | 8.3 | 102660 |
| 14 | Ii | 60 | 3.00 | 18.35 | 7.4 | 89260 |
| 15 | Ii | 60 | 3.00 | 38.69 | 6.5 | 80940 |
| 16 | MMA Dimer | 60 | 3.00 | 0.00 | 10.5 | 120010 |
| 17 | MMA Dimer | 60 | 3.00 | 12.50 | 7.0 | 59855 |
| 18 | MMA Dimer | 60 | 3.00 | 25.00 | 5.8 | 41220 |
| 19 | MMA Dimer | 60 | 3.00 | 49.88 | 5.7 | 27830 |

Number-average molecular weight determined by GPC, calibrated with polystyrene standards.

Example 3
Polymerization of Acrylate Esters

Polymerizations of methyl acrylate (MA) (or ethyl acrylate, EA) were carried out using a stock solution prepared from α,α'-azobisisobutyronitrile (6.34 mg) and distilled thiophene-free benzene (25 mL). Aliquots (6 ml) were removed and added to ampoules containing freshly distilled methyl acrylate (4 mL), thiophene-free benzene (10 mL) and weighed amounts of the activated allylic malonate chain transfer agents. After degassing, the mixtures were polymerized at 60° C. for one hour; or at 80° C. for 30 minutes; or at 90° C. for 30 minutes. The volatiles were then removed on rotary evaporator and the polymers were dried under vacuum to constant weight and examined by GPC.

TABLE 3

Molecular Weight and Conversions for Acrylate Polymerizations Carried Out in the Presence of Chain Transfer Agents (CTA).

| Entry | Monomer | CTA | Temp. (° C.) | Time (hr.) | $10^3$ [CTA]/[Monomer] | % Conv. | $M_n$ # |
|---|---|---|---|---|---|---|---|
| 1 | MA | Ia | 80 | 0.50 | 0.00 | 38.70 | 183900 |
| 2 | MA | Ia | 80 | 0.50 | 10.00 | 36.60 | 137500 |
| 3 | MA | Ia | 80 | 0.50 | 20.60 | 31.90 | 95750 |
| 4 | MA | Ia | 80 | 0.50 | 39.75 | 25.60 | 67400 |
| 5 | EA | Ib | 60 | 1.00 | 0.00 | 8.80 | 235,600 |
| 6 | EA | Ib | 60 | 1.00 | 4.33 | 4.60 | 89400 |
| 7 | EA | Ib | 60 | 1.00 | 5.87 | 3.85 | 53100 |
| 8 | EA | Ib | 60 | 1.00 | 12.81 | 2.30 | 33500 |
| 9 | MA | Ie | 60 | 1.00 | 0.00 | 26.3 | 493150 |
| 10 | MA | Ie | 60 | 1.00 | 3.73 | 25.3 | 467300 |
| 11 | MA | Ie | 60 | 1.00 | 14.67 | 21.8 | 362400 |
| 12 | MA | If | 60 | 1.00 | 0.00 | 28.2 | 388450 |
| 13 | MA | If | 60 | 1.00 | 9.43 | ~0.0 | 31455 |
| 14 | MA | If | 60 | 1.00 | 20.61 | ~0.0 | 8140 |
| 15 | MA | If | 60 | 1.00 | 34.18 | ~0.0 | 5810 |
| 16 | MA | If | 80 | 0.50 | 0.00 | 46.0 | 133300 |
| 17 | MA | If | 80 | 0.50 | 8.70 | 0.39 | 22630 |
| 18 | MA | If | 80 | 0.50 | 18.10 | 1.60 | 11540 |
| 19 | MA | If | 80 | 0.50 | 34.44 | ~0.0 | 4375 |
| 20 | MA | Ig | 60 | 1.00 | 0.00 | 21.44 | 657800 |
| 21 | MA | Ig | 60 | 1.00 | 8.84 | 0.47 | 13260 |
| 22 | MA | Ig | 60 | 1.00 | 21.32 | 0.14 | 4885 |
| 23 | MA | Ig | 60 | 1.00 | 37.33 | 0.0 | 3495 |
| 24 | MA | Ig | 80 | 0.50 | 0.00 | 17.36 | 187500 |
| 25 | MA | Ig | 80 | 0.50 | 9.43 | 0.30 | 7960 |
| 26 | MA | Ig | 80 | 0.50 | 20.73 | 0.21 | 3860 |
| 27 | MA | Ig | 80 | 0.50 | 38.79 | 0.12 | 2560 |
| 28 | MA | Ih | 60 | 1.00 | 0.00 | 20.5 | 926632 |
| 29 | MA | Ih | 60 | 1.00 | 6.54 | 22.6 | 66231 |
| 30 | MA | Ih | 60 | 1.00 | 13.30 | 27.5 | 37180 |
| 31 | MA | Ih | 60 | 1.00 | 26.50 | 12.9 | 21243 |
| 32 | MA | Ih | 80 | 0.50 | 0.00 | 40.6 | 176925 |
| 33 | MA | Ih | 80 | 0.50 | 6.91 | 38.3 | 48525 |
| 34 | MA | Ih | 80 | 0.50 | 13.30 | 32.1 | 26285 |
| 35 | MA | Ih | 80 | 0.50 | 26.50 | 28.4 | 16074 |
| 36 | MA | Ii | 60 | 1.00 | 0.00 | 23.4 | 739090 |
| 37 | MA | Ii | 60 | 1.00 | 7.49 | 3.2 | 151740 |
| 38 | MA | Ii | 60 | 1.00 | 14.29 | 1.7 | 98120 |
| 39 | MA | Ii | 60 | 1.00 | 29.24 | 0.2 | 52940 |
| 40 | MA | Ii | 90 | 0.50 | 0.00 | 55.6 | 83145 |
| 41 | MA | Ii | 90 | 0.50 | 6.93 | 20.9 | 46055 |
| 42 | MA | Ii | 90 | 0.50 | 14.91 | 16.4 | 28680 |
| 43 | MA | Ii | 90 | 0.50 | 28.99 | 14.9 | 18100 |

Number-average molecular weight determined by GPC, calibrated with polystyrene standards.

Example 4

Polymerization of Vinyl Acetate

Polymerizations of vinyl acetate (VAc) were carried out under vacuum at 60° C. for one hour or at 80° C. for one hour using the following procedure. α,α'-Azobis isobutyronitrile (20.5 mg) was dissolved in freshly distilled vinyl acetate (25 mL). Aliquots (4 mL) were removed and added to ampoules containing weighed amounts of the chain transfer agents. After the polymerization, the volatiles were removed and the polymers were dried and examined as before.

TABLE 4

Molecular Weights and Conversions for Vinyl Acetate Polymerizations Carried Out in the Presence of Chain Transfer Agents (CTA)

| Entry | CTA | Temp. (° C.) | Time (hr.) | $10^3$ [CTA]/[Monomer] | % Conv. | Mn # |
|---|---|---|---|---|---|---|
| 1 | Ie | 80 | 1.00 | 0.00 | 60.2 | 62700 |
| 2 | Ie | 80 | 1.00 | 1.87 | 29.9 | 54700 |
| 3 | Ie | 80 | 1.00 | 3.72 | 18.9 | 38300 |
| 4 | Ie | 80 | 1.00 | 7.43 | 12.6 | 25900 |
| 5 | Ig | 60 | 1.00 | 0.00 | 5.37 | 193500 |
| 6 | Ig | 60 | 1.00 | 12.90 | 0.08 | 8200 |
| 7 | Ig | 60 | 1.00 | 23.90 | 0.02 | 5740 |
| 8 | Ig | 60 | 1.00 | 39.10 | 0.03 | 3260 |

Polystyrene standard equivalent number-average molecular weight.

Table 5 summarizes the results of chain transfer constants in polymerizations of common monomers using the allylic chain transfer agents [(Ia), (Ib), (Ic), (Ie), (If), (Ig) and (Ih)].

TABLE 5

Chain Transfer Constants (Cx) for Polymerizations of Common Monomers in the Presence of Allylic Malonate Transfer Agents and MMA Dimer

| CTA | Monomer | Conditions | Chain Transfer Constants ($C_x$) |
|---|---|---|---|
| Ia | MMA | 60° C. | 0.004 |
|  | MA | 80° C. | 0.020 |
|  | Sty | 60° C. | 0.004 |
| Ib | MMA | 60° C. | 0.015 |
|  | Sty | 60° C. | 0.148 |
|  | EA | 60° C. | 0.203 |
| MMA Dimer | BMA | 60° C. | 0.007 |
|  | EA | 60° C. | 0.120 |
|  | Sty | 60° C. | 0.057 |
| Ic | MMA | 60° C. | 0.004 |
| Ie | VAc | 80° C. | 0.274 |
|  | MA | 60° C. | 0.005 |
| If | MMA | 60° C. | 0.060 |
|  | MA | 60° C. | 0.450 |
|  | MA | 80° C. | 0.560 |
| Ig | MMA | 60° C. | 0.040 |
|  | MA | 60° C. | 0.670 |
|  | MA | 80° C. | 0.850 |
|  | VAc | 60° C. | 0.010 |
| Ih | MA | 60° C. | 0.150 |
|  | MA | 80° C. | 0.180 |
|  | Sty | 60° C. | 0.150 |
| Ii | MMA | 60° C. | 0.029 |
|  | MA | 60° C. | 0.053 |
|  | MA | 90° C. | 0.130 |
|  | Sty | 60° C. | 0.009 |

Example 5

Polymerization of Styrene

A multi-necked reactor was equipped with a stirrer, thermocouple, and condenser. The reactor was held under nitrogen positive pressure and the following ingredients were used.

| Part 1 | |
|---|---|
| Styrene | 2 ml |
| MBK | 4 ml |
| Transfer agent (Ib) | 370 mg |
| Part 2 | |
| Styrene | 8 ml |

-continued

| | |
|---|---|
| MEK Part 3 | 12 ml |
| AIBN | 14 mg |
| MEK Part 4 | 2 ml |
| MEK | 2 ml |

Part 1 was charged to the reactor and heated to 80° C. When the temperature stabilized at 80° C., part 2 (the monomer feed) was charged to the reactor concurrently with part 3 (the initiator feed) over 90 minutes via a syringe pump. Then part 4 was charged to the reactor as a single shot feed to rinse the syringe pump and the reaction mixture was held at 80° C. for further 120 minutes. The solvent and unreacted monomer were then distilled. The result is summarized in Table 6.

TABLE 6

| | CTA (Ib) | $M_n$ | $M_w$ | Dispersity |
|---|---|---|---|---|
| Control | 0 | 20400 | 39350 | 1.93 |
| Example 5 | 370 mg | 14900 | 29600 | 1.94 |

Examples 6 to 8
Polymerization of n-Butyl Methacrylate/Hydroxypropyl Acrylate

A multi-necked reactor was equipped with a stirrer, thermocouple, and condenser. The reactor was held under nitrogen positive pressure and following ingredients were used in three separate polymerizations.

| PART | INGREDIENTS | Example 6 | Example 7 | Example 8 |
|---|---|---|---|---|
| I. | Xylene | 20.94 g | 20.94 g | 20.94 g |
| | Transfer Agent Ib | 0.00 g | 3.47 g | 6.94 g |
| II. | n-BMA | 51.17 g | 47.70 g | 44.23 g |
| | HPA | 18.23 g | 18.23 g | 18.23 g |
| III. | Xylene | 9.07 g | 9.07 g | 9.07 g |
| | VAZO 67 | 0.60 g | 0.60 g | 0.60 g |

Part I was charged to the reactor and heated to 90° C. When the temperature stabilized, Part II was charged to the reactor concurrently with Part III over 240 and 260 minutes, respectively. The reaction mixture was held for 60 minutes following the completion of the feeding of Part III. The monomer conversion was determined by solids analysis and molecular weight was determined by GPC. The results are summarized in Table 7.

TABLE 7

| Example Number | Wt % CTA (Ib) | $M_n$ | $M_w$ | Dispersity | Conversion |
|---|---|---|---|---|---|
| 6 | 0 (control) | 27180 | 65950 | 2.43 | 100% |
| 7 | 5.0% | 16410 | 37940 | 2.31 | 98% |
| 8 | 10.0% | 12730 | 26750 | 2.10 | 100% |

We claim:

1. A polymer formed from at least one unsaturated monomer, M, selected from the group consisting of units from acrylic esters, methacrylic esters, vinyl esters, vinyl aromatics and unsaturated hydrocarbons, having the formula:

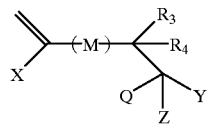

wherein:

X is selected from hydrogen; CN; optionally substituted aryl; COOH; COOR; C(O)NHR$^6$; C(O)NR$^7$R$^8$; and halogen;

Q is selected from COOR$^1$; CN; C(O)NR$^7$R$^8$;

Y is selected from hydrogen; $C_1$ to $C_6$ alkyl; $C_1$ to $C_6$ alkyl substituted with one or more substituents selected from hydroxy, amino, $C_1$ to $C_6$-alkoxy, $C_1$ to $C_6$ alkoxycarbonyl, halogen, CN, and optionally substituted aryl; $C_1$ to $C_6$ alkenyl; and $C_1$ to $C_6$ alkynyl;

Z is selected from COOR$^2$; CN; C(O)NR$^7$R$^8$; and optionally substituted aryl;

R$^3$, R$^4$ are the same or different and are selected from hydrogen, $C_1$ to $C_4$ alkyl and halogen; together with the carbon atom to which they are attached form part of a carbocyclic or heterocyclic ring structure;

R is selected from $C_1$ to $C_{18}$ alkyl; $C_1$ to $C_{12}$ alkyl substituted with one or more substituents selected from hydroxy, amino, $C_1$ to $C_6$ alkoxy, phenyl, halogen, NCO, CN, and COOR$^5$;

R$^1$, and R$^2$ are the same or different and are selected from $C_1$ to $C_{18}$ alkyl; $C_1$ to $C_{12}$ alkyl substituted with one or more substituents selected from hydroxy, $C_1$ to $C_6$ acyloxy, $C_1$ to $C_6$ alkoxy, amino, halogen, Si(R$^9$)$_3$, Si(OR$^9$)$_3$, optionally substituted aryl, CN, NCO;

R$^5$ is selected from hydrogen and $C_1$ to $C_6$ alkyl;

R$^6$ is selected from hydrogen, and $C_1$ to $C_{18}$ alkyl;

R$^7$ and R$^8$ are the same or different and are selected from $C_1$ to $C_{18}$ alkyl; and R$^9$ is selected from the group consisting of $C_1$ to $C_{18}$ alkyl; $C_1$ to $C_{18}$ cycloalkyl; and optionally substituted aryl.

2. A polymer according to claim 1:

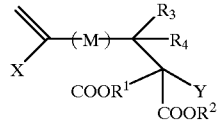

wherein:

X is selected from hydrogen; CN; optionally substituted aryl; COOH; COOR; C(O)NHR$^6$; C(O)NR$^7$R$^8$; and halogen;

Y is selected from hydrogen; $C_1$ to $C_6$ alkyl; $C_1$ to $C_6$ alkyl substituted with one or more substituents selected from hydroxy, amino, $C_1$ to $C_6$ alkoxy, $C_1$ to $C_6$ alkoxycarbonyl, halogen, CN, optionally substituted aryl; $C_1$ to $C_6$ alkenyl; $C_1$ to $C_6$ alkynyl;

R$^1$, and R$^2$ are the same or different and are selected from $C_1$ to $C_{18}$ alkyl; $C_1$ to $C_{12}$ alkyl substituted with a substituent selected from hydroxy, $C_1$ to $C_6$ acyloxy, $C_1$ to $C_6$ alkoxy, amino, halogen, optionally substituted aryl, CN, and NCO; and R$^3$, and R$^4$ are the same or different and are selected from hydrogen, $C_1$ to $C_4$ alkyl, and halogen.

3. A polymer according to claim 1:

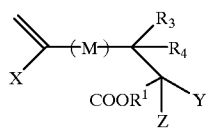

wherein Z is substituted or unsubstituted aryl.

4. A polymer of claim 1 wherein at least one monomer is selected from the group consisting of methyl acrylate, ethyl acrylate, butyl acrylate, 2-ethylhexyl acrylate, methyl methacrylate, ethyl methacrylate, n-butyl methacrylate, 2-ethylhexyl methacrylate, vinyl acetate, styrene, p-chloromethylstyrene, 2-vinylpyridine, 4-vinylpyridine, N-vinylpyrrolidone, vinyl halide of the formula $CH_2=CHX$ where X is Cl or F, vinylidene halide of the formula $CH_2=CX_2$ wherein X is independently Cl or F, vinyl ethers $CH_2=CHOR$ where R is alkyl, allyl ether, allyl carbonate, and diallyl carbonate.

5. A polymer of claim 2 wherein at least one monomer is selected from the group consisting of methyl acrylate, ethyl acrylate, butyl acrylate, 2-ethylhexyl acrylate, methyl methacrylate, ethyl methacrylate, n-butyl methacrylate, 2-ethylhexyl methacrylate, vinyl acetate, styrene, p-chloromethylstyrene, 2-vinylpyridine, 4-vinylpyridine, N-vinylpyrrolidone, vinyl halide of the formula $CH_2=CHX$ where X is Cl or F, vinylidene halide of the formula $CH_2=CX_2$ wherein X is independently Cl or F, vinyl ethers $CH_2=CHOR$ where R is alkyl, allyl ether, allyl carbonate, and diallyl carbonate.

6. A polymer of claim 3 wherein at least one monomer is selected from the group consisting of methyl acrylate, ethyl acrylate, butyl acrylate, 2-ethylhexyl acrylate, methyl methacrylate, ethyl methacrylate, n-butyl methacrylate, 2-ethylhexyl methacrylate, vinyl acetate, styrene, p-chloromethylstyrene, 2-vinylpyridine, 4-vinylpyridine, N-vinylpyrrolidone, vinyl halide of the formula $CH_2=CHX$ where X is Cl or F, vinylidene halide of the formula $CH_2=CX_2$ wherein X is independently Cl or F, vinyl ethers $CH_2=CHOR$ where R is alkyl, allyl ether, allyl carbonate, and diallyl carbonate.

7. A polymer of claim 1 wherein M comprises methacrylate ester units.

8. A polymer of claim 7 wherein M comprises methyl methacrylate units.

9. A polymer of claim 7 wherein M comprises n-butyl methacrylate and hydroxypropyl acrylate units.

10. A polymer according to claim 1 wherein M comprises acrylic ester units.

11. A polymer according to claim 10 wherein M comprises methyl acrylate units.

12. A polymer according to claim 1 wherein M comprises vinyl ester units.

13. A polymer according to claim 12 wherein M comprises vinyl acetate units.

14. A polymer according to claim 1 wherein M comprises vinyl aromatic units.

15. A polymer according to claim 14 wherein M comprises styrene units.

16. A polymer according to claim 1 wherein M comprises unsaturated hydrocarbon units.

17. A polymer formed from the free radical initiated polymerization of ethylenically unsaturated monomers using a chain transfer agent of the formula (I) below:

Formula (I)

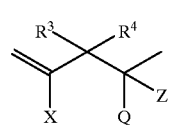

wherein,

X is selected from the group consisting of hydrogen; CN; optionally substituted aryl; COOH; COOR; C(O)NHR$^6$; C(O)NR$^7$R$^8$; and halogen;

Q is selected from the group consisting of COOR$^1$; CN; and C(O)NR$^7$R$^8$;

Y is selected from the group consisting of hydrogen; $C_1$ to $C_6$ alkyl; $C_1$ to $C_6$ alkyl substituted with one or more substituents selected from the group consisting of hydroxy, amino, $C_1$ to $C_6$-alkoxy, $C_1$ to $C_6$ alkoxycarbonyl, halogen, CN, and optionally substituted aryl; $C_1$ to $C_6$ alkenyl; and $C_1$ to $C_6$ alkynyl;

Z is selected from the group consisting of COOR$^2$; CN; C(O)NR$^7$R$^8$; and optionally substituted aryl;

R$^3$, R$^4$ are the same or different and are selected from the group consisting of hydrogen, $C_1$ to $C_4$ alkyl, and halogen; together with the carbon atom to which they are attached form part of a carbocyclic or heterocyclic ring structure;

R is selected from the group consisting of $C_1$ to $C_{18}$ alkyl; and $C_1$ to $C_{12}$ alkyl substituted with one or more substituents selected from the group consisting of hydroxy, amino, $C_1$ to $C_6$ alkoxy, phenyl, halogen, NCO, CN, and COOR$^5$;

R$^1$, and R$^2$ are the same or different and are selected from the group consisting of $C_1$ to $C_{18}$ alkyl; and $C_1$ to $C_{12}$ alkyl substituted with one or more substituents selected from the group consisting of hydroxy, $C_1$ to $C_6$ acyloxy, $C_1$ to $C_6$ alkoxy, amino, halogen, Si(R$^9$)$_3$, Si(OR$^9$)$_3$, optionally substituted aryl, CN, and NCO;

R$^5$ is selected from the group consisting of hydrogen and $C_1$ to $C_6$ alkyl;

R$^6$ is selected from the group consisting of hydrogen, and $C_1$ to $C_{18}$ alkyl;

R$^7$ and R$^8$ are the same or different and are selected from $C_1$ to $C_{18}$ alkyl; and R$^9$ is selected from the group consisting of $C_1$ to $C_{18}$ alkyl; $C_1$ to $C_{18}$ cycloalkyl; and optionally substituted aryl.

* * * * *